US007491847B2

(12) United States Patent
Frenkel et al.

(10) Patent No.: US 7,491,847 B2
(45) Date of Patent: Feb. 17, 2009

(54) METHODS FOR ISOLATING PROPARGYLATED AMINOINDANS

(75) Inventors: Anton Frenkel, Netanya (IL); Ramy Lidor-Hadas, Kfar Saba (IL); Eduard Gurevich, Petach-Tikva (IL); Gsan Attili, Tire (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 22 days.

(21) Appl. No.: 11/600,561

(22) Filed: Nov. 15, 2006

(65) Prior Publication Data

US 2007/0112217 A1 May 17, 2007

Related U.S. Application Data

(60) Provisional application No. 60/738,163, filed on Nov. 17, 2005.

(51) Int. Cl.
*C07C 211/42* (2006.01)
*C07C 271/44* (2006.01)
*A61K 31/21* (2006.01)
*A61K 31/135* (2006.01)

(52) U.S. Cl. .................. 564/308; 560/163; 514/510; 514/647

(58) Field of Classification Search .................. None
See application file for complete search history.

(56) References Cited

U.S. PATENT DOCUMENTS

| | | | |
|---|---|---|---|
| 3,513,249 | A | 5/1970 | Gittos et al. |
| 5,387,612 | A | 2/1995 | Youdim et al. |
| 5,444,095 | A | 8/1995 | Tatton et al. |
| 5,453,446 | A | 9/1995 | Youdim et al. |
| 5,457,133 | A | 10/1995 | Youdim et al. |
| 5,486,541 | A | 1/1996 | Sterling et al. |
| 5,519,061 | A | 5/1996 | Youdim et al. |
| 5,532,415 | A | 7/1996 | Youdim et al. |
| 5,576,353 | A | 11/1996 | Youdim et al. |
| 5,599,991 | A | 2/1997 | Youdim et al. |
| 5,668,181 | A | 9/1997 | Youdim et al. |
| 5,744,500 | A | 4/1998 | Youdim et al. |
| 5,767,164 | A | 6/1998 | Tatton et al. |
| 5,786,390 | A | 7/1998 | Youdim et al. |
| 5,844,003 | A | 12/1998 | Tatton et al. |
| 5,891,923 | A | 4/1999 | Youdim et al. |
| 6,126,968 | A | 10/2000 | Peskin et al. |
| 6,277,886 | B1 | 8/2001 | Levy et al. |
| 6,316,504 | B1 | 11/2001 | Youdim et al. |
| 6,462,222 | B1 | 10/2002 | Chorev et al. |
| 6,630,514 | B2 | 10/2003 | Youdim et al. |
| 6,635,667 | B2 | 10/2003 | Thomas |
| 6,956,060 | B2 | 10/2005 | Youdim et al. |
| 2004/0010038 | A1 | 1/2004 | Blaugrund et al. |
| 2004/0052843 | A1 | 3/2004 | Lerner et al. |
| 2004/0127577 | A1 | 7/2004 | Blaugrund et al. |
| 2006/0018957 | A1 | 1/2006 | Lerner et al. |
| 2006/0094783 | A1 | 5/2006 | Youdim et al. |
| 2006/0188581 | A1 | 8/2006 | Peskin |
| 2007/0100001 | A1 | 5/2007 | Youdim et al. |
| 2007/0232700 | A1 | 10/2007 | Blaugrund et al. |
| 2008/0146676 | A1 | 6/2008 | Frenkel et al. |
| 2008/0161408 | A1 | 7/2008 | Frenkel et al. |

FOREIGN PATENT DOCUMENTS

| | | |
|---|---|---|
| EP | 0 538 134 | 4/1993 |
| EP | 0 436 492 | 6/1994 |
| GB | 1003686 | 9/1965 |
| WO | WO 95/11016 | 4/1995 |
| WO | WO 95/18617 | 7/1995 |
| WO | WO 96/37199 | 11/1996 |
| WO | WO 97/12583 | 4/1997 |
| WO | WO 98/02152 | 1/1998 |
| WO | WO 03072055 | 9/2003 |
| WO | WO 2004/045515 | 6/2004 |
| WO | 2006057912 | 1/2006 |
| WO | WO 2006/057912 | 6/2006 |
| WO | 2006091656 | 8/2006 |

OTHER PUBLICATIONS

Polymorphism in Molecular Crystals, Bernstein, J., Oxford University Press, 2002, chapter 2, section, 2.4.1, (p. 46-49).*
Finberg and Youdim (1985) "Mod. of Blood Pressure and Nictitating Membrane Resp. to Sympathetic Amines by Selective Monoamine Oxidase Inhibitors" Brit. J. Pharmac. 85(2):541-6.
Mendlewicz J. and Youdim, MBH Brit. J. Psychiat. (1983) 142:508-511.
Youdim MBH, et al. Progress in Medicinal Chemistry (1984) 21:138-167.
Youdim MBH, et al., "Rasagiline (N-propargyl-1R(+)-aminoindan), a selective and potent inhibitor of mitochondrial monoamine oxidase B", Br. J. Pharmacol., 2001, 132:500-6.
Youdim et al. in Handbook of Experimental Pharmacology vol. 90/I (1988) Chapter 3, Trendlenburg and Weiner, eds.
U.S. Appl. No. 12/002,076, filed Dec. 13, 2007, Frenkel et al.
U.S. Appl. No. 12/002,082, filed Dec. 13, 2007, Frenkel et al.
International Search Report and the Written Opinion of the International Searching Authority for PCT/US2006/044327, published Feb. 6, 2008.
Finberg et al. (1981) "Selective Irreversible Propargyl Derivative Inhibitors of Monoamine Oxidase (MAO) without the Cheese Effect" Chem. Abstracts, 1981, 94:202499.
Finberg et al. (1985) "Modification of Blood Pressure and Nictitating Membrane Response to Sympathetic Amides by Selective Monoamide Oxidase Inhibitors Types A and B, in the Cat" Chem. Abstracts, 1985, 103:81618.
Bernstein J., Polymorphism in Molecular Crystal, Oxford University Press, 2002, Chapter 2, Section 2.4.1, p. 46-49.
U.S. Appl. No. 11/791,684, filed May 24, 2007, Patashnick et al.
U.S. Appl. No. 12/223,794, filed Aug. 7, 2008, Poewe et al.
U.S. Appl. No. 12/283,946, filed Sep. 16, 2008, Lendvai et al.
U.S. Appl. No. 12/231,601, filed Sep. 3, 2008, Oron et al.

* cited by examiner

*Primary Examiner*—Brian J Davis
(74) *Attorney, Agent, or Firm*—John P. White; Cooper & Dunham LLP

(57) ABSTRACT

A process for isolating from a reaction mixture a salt of a mono-propargylated aminoindan, a process for isolating from a reaction mixture a crystalline diastereomeric salt of a mono-propargylated aminoindan, and a process for isolating from a reaction mixture a salt of enantiomerically pure N-propargyl-1-aminoindan or a salt of enantiomerically pure 6-(N-methyl, N-ethyl-carbamoyloxy)-N'-propargyl-1-aminoindan. The corresponding products are also disclosed.

37 Claims, 7 Drawing Sheets

* R+S aminoindan (AI); R+S (PAI); and N,N bispropargyl aminoindan (di-PAI)

METHODS FOR ISOLATING PROPARGYLATED AMINOINDANS

This application claims benefit of U.S. Provisional Application No. 60/738,163, filed Nov. 17, 2005 and the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

FIELD OF THE INVENTION

The present invention concerns methods of isolation of secondary propargylated aminoindan derivatives from a reaction mixture.

BACKGROUND OF THE INVENTION

The secondary propargylated aminoindan rasagiline has been shown to be a selective inhibitor of MAO-B, and useful in treating Parkinson's disease and various other conditions. U.S. Pat. No. 5,532,415 discloses rasagiline (R(+)-N-propargyl-1-aminoindan (R(+)PAI)), its preparation, and various pharmaceutically acceptable salts thereof.

Another secondary propargylated aminoindan is R(+)-6-(N-methyl,N-ethyl-carbamoyloxy)-N'-propargyl-1-aminoindan, also known as (3R)-3-(prop-2-ynylamino)-2,3,-dihydro-1H-inden-5-yl ethylmethylcarbamate, which has been disclosed in PCT International Application Publication No. WO98/27055 (U.S. Pat. No. 6,303,650, issued Oct. 16, 2001 to Chorev). In addition, its preparation and its salts are disclosed, including the 1/2 L-tartrate salt. The 1/2 L-tartrate salt has been given the nonproprietary name ladostigil tartrate. Its CAS registry number is 209394-46-7. PCT International Application Publication No. WO98/27055 also discloses aminoindans having the formula:

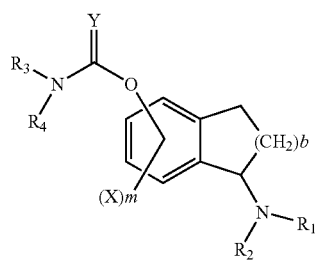

wherein b is 1 or 2; m is 0-3; Y is O or S; X is halo; $R_1$ is hydrogen or $C_{1-4}$ alkyl; $R_2$ is hydrogen, $C_{1-4}$ alkyl, or optionally substituted propargyl; and $R_3$ and $R_4$ are each independently, $C_{1-8}$ alkyl, $C_{6-12}$ aryl, $C_{6-12}$ aralkyl, each optionally halo substituted, or hydrogen. These compounds have been disclosed as being useful to treat depression, Attention Deficit Disorder (ADD), Attention Deficit and Hyperactivity Disorder (ADHD), Tourett's Syndrome, Alzheimer's Disease and other dementias.

These aminoindans have a chiral carbon to which the amino group is attached. Thus, in order to obtain enantiomerically pure compounds, when a racemic starting material is used enantiomeric resolution of these compounds is needed. This is normally the case when racemic 1-aminoindan is used as the starting material. U.S. Pat. No. 5,532,415 discloses that enantiomerically pure aminoindan derivatives may be obtained by optical resolution of racemic mixtures of R- and S-enantiomers of propargyl aminoindan derivatives. Such a resolution can be accomplished by any conventional resolution method well known to a person skilled in the art, such as those described in J. Jacques, A. Collet and S. Wilen, "Enantiomers, Racemates and Resolutions," Wiley, N.Y. (1981). For example, the resolution may be carried out by preparative chromatography on a chiral column.

U.S. Pat. No. 5,532,415 describes how an enantiomerically pure propargyl aminoindan can also be prepared directly from the optically active R-enantiomer of 1-aminoindan by reaction with propargyl bromide or propargyl chloride or a propargyl sulfonate ester in the presence of an organic or inorganic base, and optionally in the presence of a suitable solvent. Suitable organic or inorganic bases for use in such reaction include, by way of example, triethylamine, pyridine, alkali metal carbonates, and bicarbonates. If the reaction is conducted in the presence of a solvent, the solvent may be chosen from, e.g., toluene, methylene chloride, and acetonitrile.

All of the aminoindan derivative separation methods mentioned in the prior art have their respective shortcomings, however. Chromatography is difficult to scale up because of the large quantities of solvents used, which are difficult to dispose of. Distillation is virtually impossible because of the high boiling points of the aminoindan derivatives. For example, even the primary aminoindan derivative 1-aminoindan boils at between 95° C. and 97° C. at 13 mbar, and at the same pressure the secondary and tertiary propargylated aminoindan derivatives will require higher temperature which is not industrially feasible. Selective extraction is also disadvantageous in that large amounts of solvent are required and large amounts of acidic solvents are produced which are difficult to dispose of. In addition, many steps are required for extraction, re-extraction and isolation of secondary propargyl aminoindan free base derivatives. An additional step of salt formation must be added after isolation of the secondary propargyl aminoindan free base derivatives in order to attain secondary propargyl aminoindan derivative salts.

SUMMARY OF THE INVENTION

The subject invention provides a process for isolating from a reaction mixture a salt of a mono-propargylated aminoindan having the structure

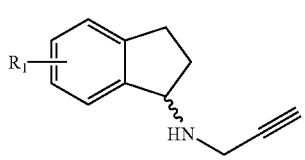

wherein $R_1$ is H, hydroxyl, alkoxy or

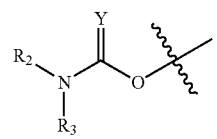

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a primary aminoindan having the structure

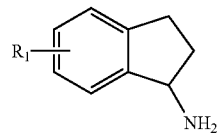

wherein $R_1$ is defined as above, and a tertiary aminoindan having the structure

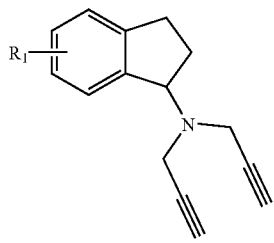

the process comprising
  a) adding an acid to the reaction mixture;
  b) crystallizing the mono-propargylated aminoindan under conditions suitable for the formation of a crystalline salt of the mono-propargylated aminoindan; and
  c) recovering the crystalline salt of the mono-propargylated aminoindan, wherein the process is performed without addition of an organic solvent.

The subject invention also provides a process for isolating from a reaction mixture a diastereomeric salt of a mono-propargylated aminoindan having the structure

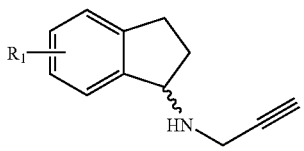

wherein $R_1$ is H, hydroxyl, alkoxy or

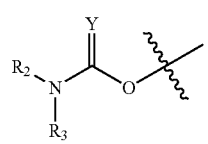

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a racemic primary aminoindan having the structure

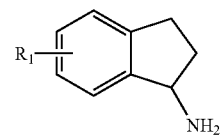

wherein $R_1$ is defined as above, and a racemic tertiary aminoindan having the structure

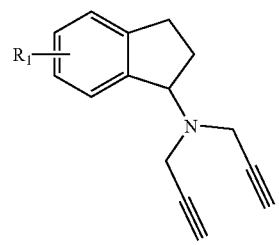

said process comprising
  a) adding a first acid to the reaction mixture in an amount sufficient to form a crystalline acid addition salt of the primary aminoindan;
  b) removing the crystalline acid addition salt said of the primary aminoindan from the reaction mixture, thereby separating the primary aminoindan from the reaction mixture;
  c) adding a second acid to the reaction mixture under conditions suitable for the formation of the crystalline salt of mono-propargylated aminoindan; and
  d) recovering the crystalline salt of the mono-propargylated aminoindan.

The subject invention also provides a process for isolating from a reaction mixture a diastereomeric salt of a mono-propargylated aminoindan having the structure

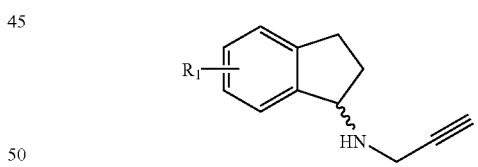

wherein $R_1$ is H, hydroxyl, alkoxy or

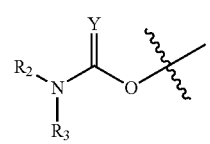

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a racemic primary aminoindan having the structure

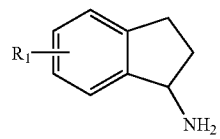

wherein R1 is defined as above, and a racemic tertiary aminoindan having the structure

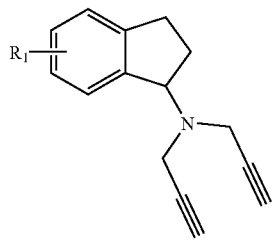

said process comprising
a) adding a chiral acid to the reaction mixture in an amount equivalent to the mono-propargylated aminoindan derivative to form a crude diastereomeric salt of the monopropargylated aminoindan;
b) separating the crude diastereomeric salt of the mono-propargylated aminoindan from the reaction mixture;
c) recrystallizing the crude diastereomeric salt of the mono-propargylated aminoindan in water to isolate crystalline diastereomeric salt of the mono-propargylated aminoindan; and
d) recovering crystalline diastereomeric salt of the mono-propargylated aminoindan.

The subject invention also provides a process for isolating from a reaction mixture a salt of enantiomerically pure N-propargyl-1-aminoindan or a salt of enantiomerically pure 6-(N-methyl,N-ethyl-carbamoyloxy)-N'-propargyl-1-aminoindan, wherein the reaction mixture further comprises a primary aminoindan having the structure

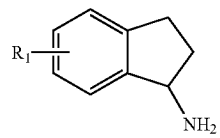

wherein $R_1$ is H or

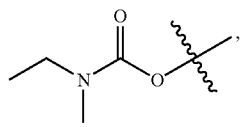

and a tertiary aminoindan having the structure

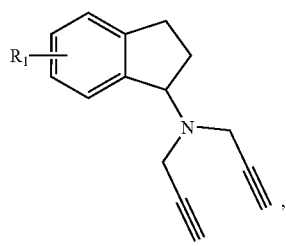

the process comprising crystallizing the salt of enantiomerically pure N-propargyl-1-aminoindan or the salt of enantiomerically pure 6-(N-methyl,N-ethyl-carbamoyloxy)-N'-propargyl-1-aminoindan,
wherein the process is performed without addition of an organic solvent.

DETAILED DESCRIPTION OF THE INVENTION

Figure 1:
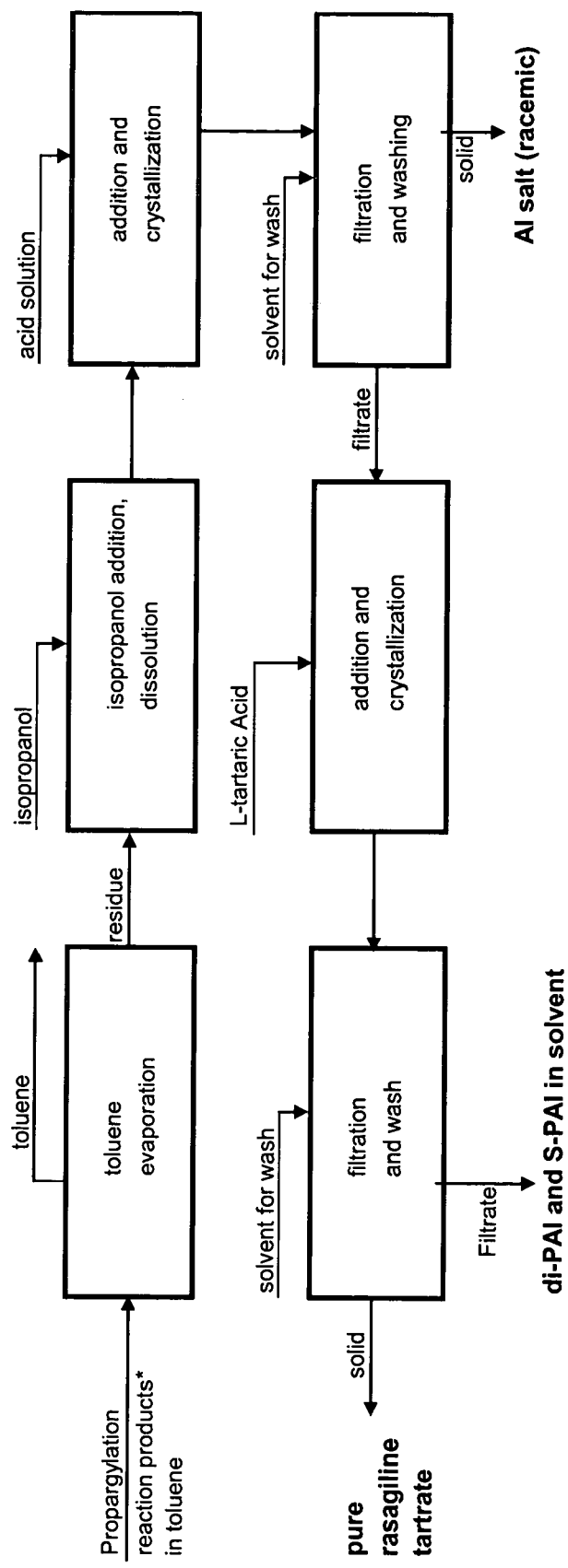
FIG. 1: Block diagram depicting rasagiline tartrate isolation via primary aminoindan crystallization.

The subject invention provides a process for isolating from a reaction mixture a salt of a mono-propargylated aminoindan having the structure

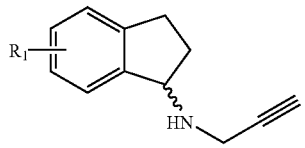

wherein $R_1$ is H, hydroxyl, alkoxy or

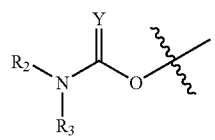

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a primary aminoindan having the structure

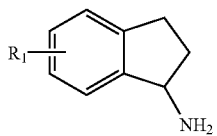

wherein $R_1$ is defined as above, and a tertiary aminoindan having the structure

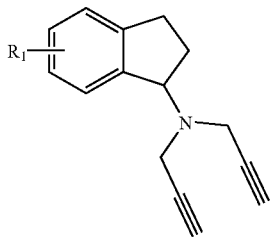

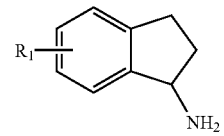

wherein $R_1$ is defined as above, and a racemic tertiary aminoindan having the structure the process comprising a) adding an acid to the reaction mixture;

b) crystallizing the mono-propargylated aminoindan under conditions suitable for the formation of a crystalline salt of the mono-propargylated aminoindan; and c) recovering the crystalline salt of the mono-propargylated aminoindan, wherein the process is performed without addition of an organic solvent.

The wavy line used in the structure of the mono-propargylated aminoindan represents a compound that is racemic, enantiomerically pure or enantiomerically enriched.

In an embodiment of the process, a) comprises:

1) adding a first acid to the reaction mixture in an amount sufficient to form a crystalline acid addition salt of the primary aminoindan; and 2) removing the crystalline acid addition salt of the primary aminoindan from the reaction mixture, thereby separating the primary aminoindan from the mono-propargylated aminoindan and the tertiary aminoindan.

In another embodiment of the process, step b) comprises addition of a second acid to the reaction mixture under conditions suitable for the formation of the crystalline salt of mono-propargylated aminoindan.

The subject invention also provides a process for isolating from a reaction mixture a diastereomeric salt of a mono-propargylated aminoindan having the structure

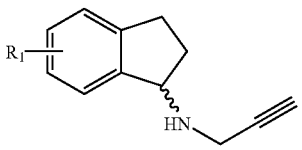

wherein $R_1$ is H, hydroxyl, alkoxy or

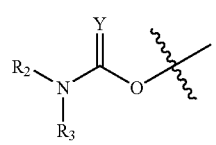

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a racemic primary aminoindan having the structure said process comprising a) adding a first acid to the reaction mixture in an amount sufficient to form a crystalline acid addition salt of the primary aminoindan;

b) removing the crystalline acid addition salt said of the primary aminoindan from the reaction mixture, thereby separating the primary aminoindan from the reaction mixture;

c) adding a second acid to the reaction mixture under conditions suitable for the formation of the crystalline salt of mono-propargylated aminoindan; and d) recovering the crystalline salt of the mono-propargylated aminoindan.

In an embodiment of the process, the first acid is added in a quench amount to the primary aminoindan in the reaction mixture.

In another embodiment of the process, the first acid is sulfuric acid or tartaric acid.

In yet another embodiment of the process, the solvent in the reaction mixture is isopropanol.

In a further embodiment of the process, the crystalline acid addition salt of the primary aminoindan is removed by filtration.

The process may further comprise a step of washing the crystalline salt of the mono-propargylated aminoindan.

In yet a further embodiment of the process, step a) comprises:

1) adding a chiral acid to the reaction mixture in an amount equivalent to the mono-propargylated aminoindan to form a crude diastereomeric salt of the mono-propargylated aminoindan; and 2) separating the crude diastereomeric salt of the mono-propargylated aminoindan from the reaction mixture.

In yet a further embodiment of the process, step b) comprises recrystallization of the crude diastereomeric salt of mono-propargylated aminoindan in water.

The subject invention also provides a process for isolating from a reaction mixture a diastereomeric salt of a mono-propargylated aminoindan having the structure

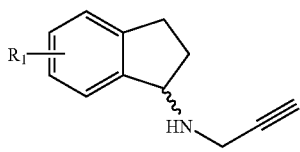

wherein $R_1$ is H, hydroxyl, alkoxy or

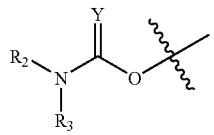

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a racemic primary aminoindan having the structure

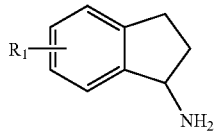

wherein R1 is defined as above, and a racemic tertiary aminoindan having the structure

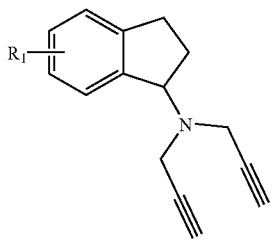

said process comprising
a) adding a chiral acid to the reaction mixture in an amount equivalent to the mono-propargylated aminoindan derivative to form a crude diastereomeric salt of the monopropargylated aminoindan;
b) separating the crude diastereomeric salt of the mono-propargylated aminoindan from the reaction mixture;
c) recrystallizing the crude diastereomeric salt of the mono-propargylated aminoindan in water to isolate crystalline diastereomeric salt of the mono-propargylated aminoindan; and
d) recovering crystalline diastereomeric salt of the mono-propargylated aminoindan.

In one embodiment of the process, $R_1$, is H.
In another embodiment of the process, $R_1$, is

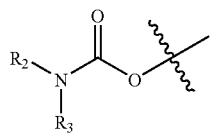

where $R_2$ is H or $C_1$-$C_4$ alkyl and $R_3$ is $C_1$-$C_4$ alkyl.
In yet another embodiment of the process, $R_2$ is methyl and $R_3$ is ethyl.

In a further embodiment of the process, $R_1$ is attached to the carbon at the 6 position.

In yet a further embodiment of the process, the chiral acid is L-tartaric acid and the diastereomeric salt is the L-tartrate salt.

In yet a further embodiment of the process, the mono-propargylated aminoindan tartrate salt is 99% pure, 98% pure, 97% pure, 95% pure or 90% pure.

In yet a further embodiment of the process, the mono-propargylated aminoindan tartrate salt is 99% enantiomerically enriched, 98% enantiomerically enriched, 97% enantiomerically enriched, 95% enantiomerically enriched or 90% enantiomerically enriched.

In yet a further embodiment of the process, the mono-propargylated aminoindan tartrate salt is ladostigil tartrate.

The process may further comprise converting the mono-propargylated aminoindan diastereomeric salt into a mesylate salt.

In a further embodiment of the process, the mono-propargylated aminoindan diastereomeric mesylate salt is rasagiline mesylate.

The subject invention also provides a process for isolating from a reaction mixture a salt of enantiomerically pure N-propargyl-1-aminoindan or a salt of enantiomerically pure 6-(N-methyl,N-ethyl-carbamoyloxy)-N'-propargyl-1-aminoindan, wherein the reaction mixture further comprises a primary aminoindan having the structure

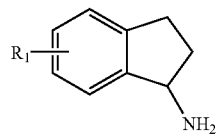

wherein $R_1$ is H or

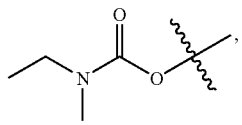

and a tertiary aminoindan having the structure

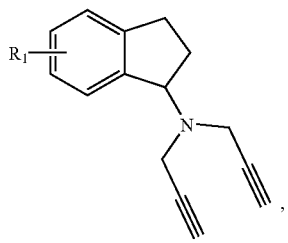

the process comprising crystallizing the salt of enantiomerically pure N-propargyl-1-aminoindan or the salt of enantiomerically pure 6-(N-methyl,N-ethyl-carbamoyloxy)-N'-propargyl-1-aminoindan,
wherein the process is performed without addition of an organic solvent.

In one embodiment of the process, the enantiomerically pure N-propargyl-1-aminoindan is R(+)-N-propargyl-1-aminoindan, and the enantiomerically pure 6-(N-methyl,N- ethyl-carbamoyloxy)-N'-propargyl-1-aminoindan is R(+)-6-(N-methyl,N-ethyl-carbamoyloxy)-N'-propargyl-1-aminoindan In another embodiment of the process, the salt of R(+)-N-propargyl-1-aminoindan is the tartrate salt and the salt of R(+)-6-(N-methyl,N-ethyl-carbamoyloxy)-N'-propargyl-1-aminoindan is the tartrate salt.

The subject invention also provides crystalline diastereomeric salt of the mono-propargylated aminoindan prepared by the processes described herein having an aspect ratio of less than 15, less than 12 or less than 10, and a pharmaceutical composition comprising the crystalline diastereomeric salt.

The subject invention also provides crystalline rasagiline tartrate salt having an aspect ratio of less than 15, less than 12 or less than 10, and a pharmaceutical composition comprising the crystalline rasagiline tartrate salt.

The reaction of racemic primary aminoindan derivatives with propargylating agents is summarized below in scheme 1.

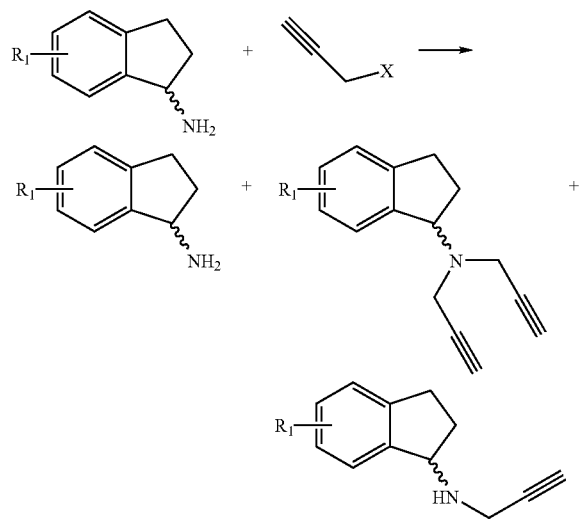

In scheme 1, $R_1$ is defined as H, hydroxyl, alkoxy or

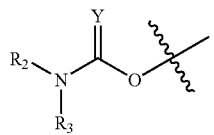

wherein Y may be O or S; $R_2$ and $R_3$ may each be, independently, $C_{1-8}$ alkyl, $C_{6-12}$ aryl, $C_{6-12}$ aralkyl, each optionally halo substituted, or hydrogen; and X may be Cl, Br, I, $PhSO_3$, $MeSO_3$, or $Me\text{-}PheSO_3$.

This reaction can also be performed with an enantiomerically pure primary amine as a starting reagent, which will result in only one secondary amine enantiomer being formed.

The reaction of aminoindan derivatives with propargylating agents is not selective. When the molar ratio of starting aminoindan derivative to propargylating agent is approximately 1:1, the reaction mixture results in a racemic mixture of the "primary" aminoindan derivatives, "secondary" or propargyl aminoindan derivatives, and "tertiary" or di-propargylated aminoindan derivatives. Adding an excess of a propargylating reagent results in a complete conversion of the starting aminoindan derivative but it increases the yield of the di-propargylated aminoindan derivative. The starting material could be recovered from the reaction mixture, but an excess of the di-propargylated aminoindan derivative should be avoided. Therefore the preferred molar ratio of propargylating reagent to starting aminoindan is 1:1.

Thus, the reaction of a racemic 1-aminoindan derivative with a propargyl chloride, bromide, or a propargyl sulfonate ester results in a mixture of unreacted primary amine derivative, a racemic mixture of the desired secondary amine derivative and the tertiary amine N,N-bispropargylamino product. The desired secondary amine, e.g., R(+)-N-propargyl-1-aminoindan, can be separated from this mixture by a conventional separation method including, by way of example, chromatography, distillation and selective extraction. After separation of the desired secondary propargylated amine derivative, salt formation and/or enantiomeric isolation can be performed. As noted, the conventional separation methods have their respective shortcomings.

Another example of a resolution method is the formation of diastereomeric salts with a chiral acid such as tartaric, malic, mandelic acid or N-acetyl derivatives of amino acids, such as N-acetyl leucine, followed by recrystallization to isolate the diastereomeric salt of the desired R enantiomer. Such a direct isolation process was attempted for the aminoindan derivatives discussed herein. Direct isolation processes are processes designed to crystallize or precipitate the desired product directly from the reaction mixture so as to avoid extra separation steps. A perspective on direct isolation processes is offered by Anderson, N., *Organic Process Research & Development*, Vol. 8, No. 2, 2004, 260-265. However, no information was previously available on how direct isolation could be applied to, or whether it would be successful in the context of the aminoindan derivatives discussed herein.

The approach undertaken for the isolation of aminoindan derivatives discussed herein involved the use of chiral acids to directly precipitate the desired product. The relative amounts of reaction products and starting materials in the aminoindan reaction mixture can be determined by readily available methods such as high pressure liquid chromatography. Once the relative amounts of reaction products and starting materials in the reaction mixture are known, the amounts of an acid needed to initiate crystallization can be calculated.

Chiral acids contain a carbon atom that is surrounded by four different groups, allowing for isomers that are non-superimposable mirror-images (leading to optical isomerism). Examples of such chiral acids include: tartaric acid, malic acid, mandelic acid or N-acetyl derivatives of amino acids, such as N-acetyl leucine. Other examples of chiral acids known in the art are disclosed in J. Jacques, A Collet and S. Wilen, "Enantiomers, Racemates and Resolutions," Wiley, New York (1981).

"Chiral acids", as used herein, are acids which when combined with a racemic mixture of an aminoindan derivative free base will form diastereomeric salts with primarily one of the enantiomers. "Diastereomeric salt", as used herein, refers to salt with two chiral centers, which is formed by mixing a racemate with a chirally-pure compound.

Initial attempts to directly isolate the aminoindan derivative were unsuccessful. Direct crystallization of one enantiomer of a secondary propargyl aminoindan derivative from the reaction mixture was attempted by adding an amount of L-tartaric acid to the reaction mixture equivalent to the amount of one of the enantiomers of secondary propargyl aminoindan derivatives. (See Examples 3, 4, and 5.) In these examples, however, pure rasagiline tartrate salt was not formed. The crude salt which was formed was contaminated with significant amounts of primary aminoindan and with (S)-PAI.

After further extensive study, it was found that final crystallization of the secondary aminoindan derivatives of interest, e.g. rasagiline and ladostigil, should not occur in the presence of primary aminiondan. Based on this finding, the process that has been developed is counterintuitive in that it removes the bulk of the primary aminoindan before final crystallization of the secondary aminoindan derivatives of interest with the chiral acid.

Two examples of the disclosed method have been named the "aminoindan crystallization method" and the "water recrystallization method".

The "aminoindan crystallization method" is represented in FIG. 1 and involves the following steps:
adding a first acid to the reaction mixture, in an equivalent amount to form a primary optionally substituted aminoindan acid addition salt,
removing the optionally substituted primary aminoindan acid addition salt from the reaction mixture,
adding L-tartaric acid to the reaction mixture to form a mono-propargylated aminoindan tartrate salt, and
removing the mono-propargylated aminoindan tartrate salt from the reaction mixture.

One of the advantages of the "aminoindan crystallization method" is that primary aminoindan derivatives of high purity are isolated and may be reused in the propargylation reaction. Another advantage is that this method requires less organic solvent than the prior art extraction method, and does not require disposal of large amounts of acidic solvents.

Figure 2:
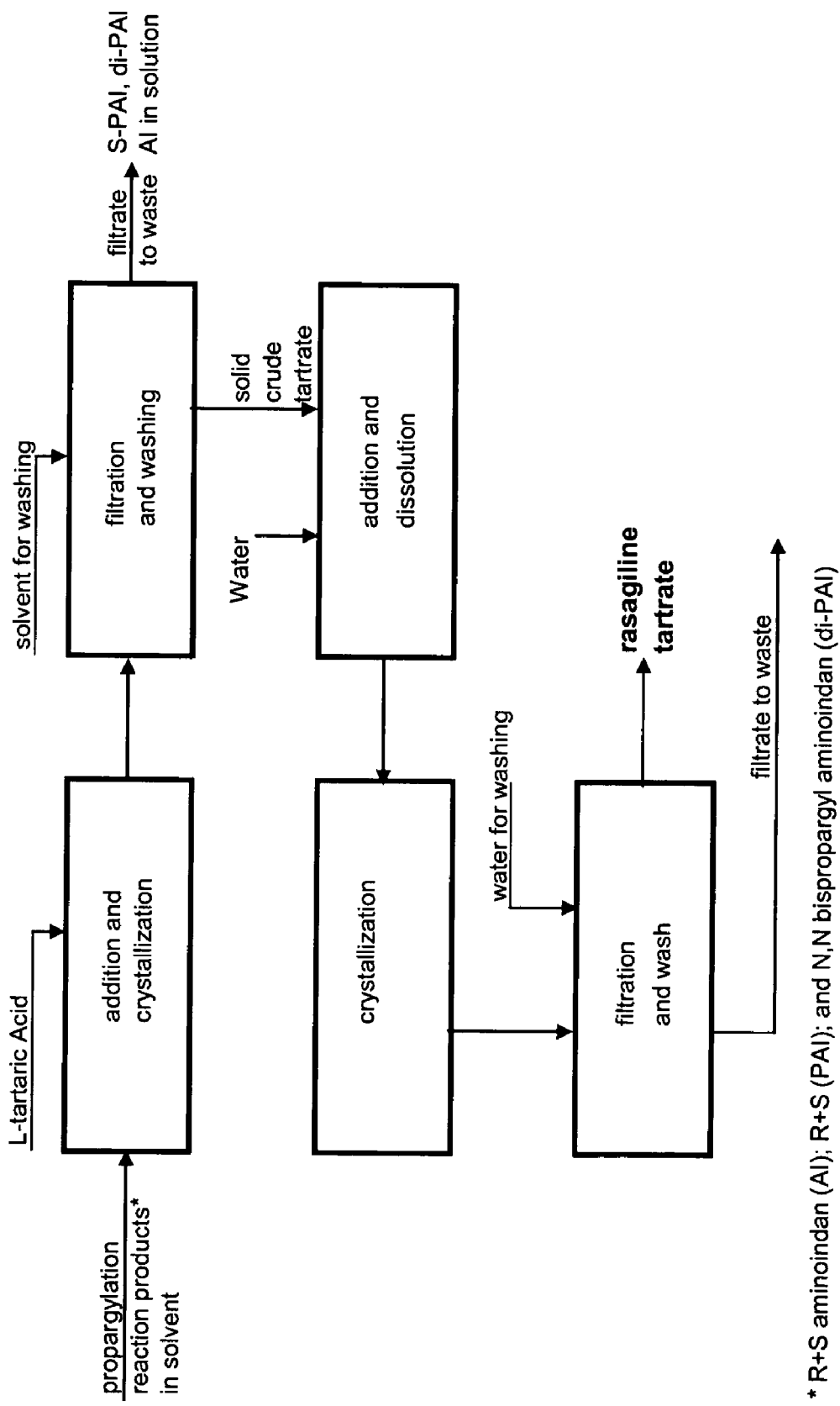
FIG. 2: Block diagram depicting rasagiline tartrate isolation via water recrystallization.
Figure 3A:
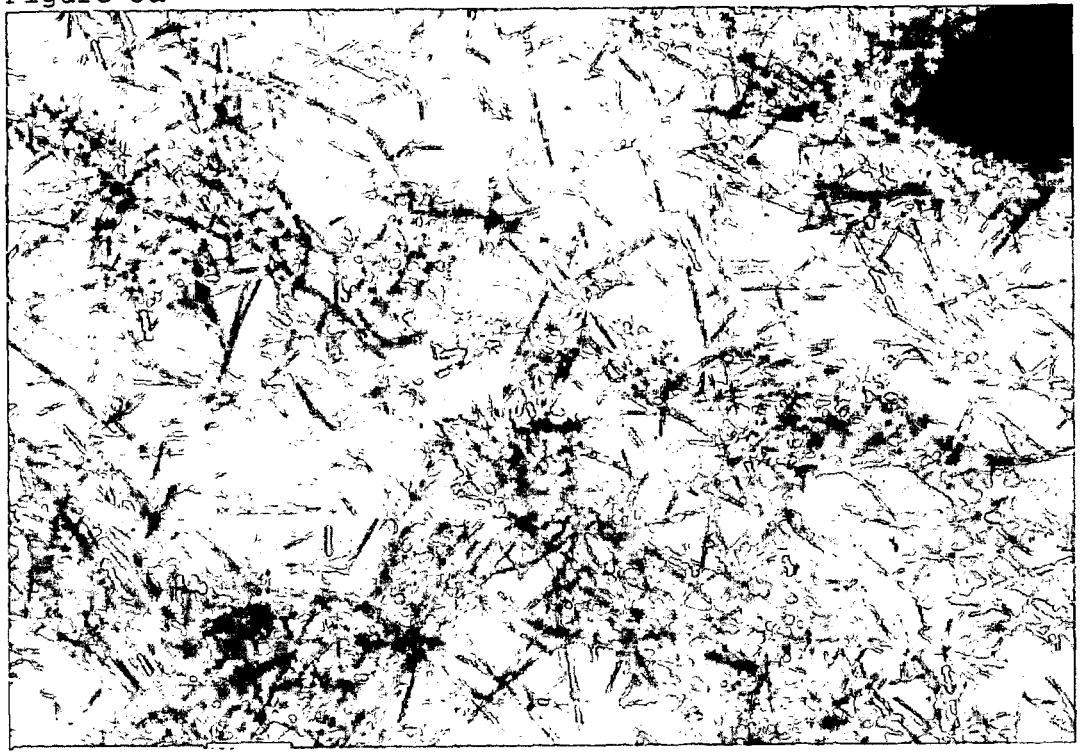
FIGS. 3a-b: Micrographs (100× and 50× magnification, respectively) of rasagiline tartrate crystals prepared according to Example 1.
Figure 3B:
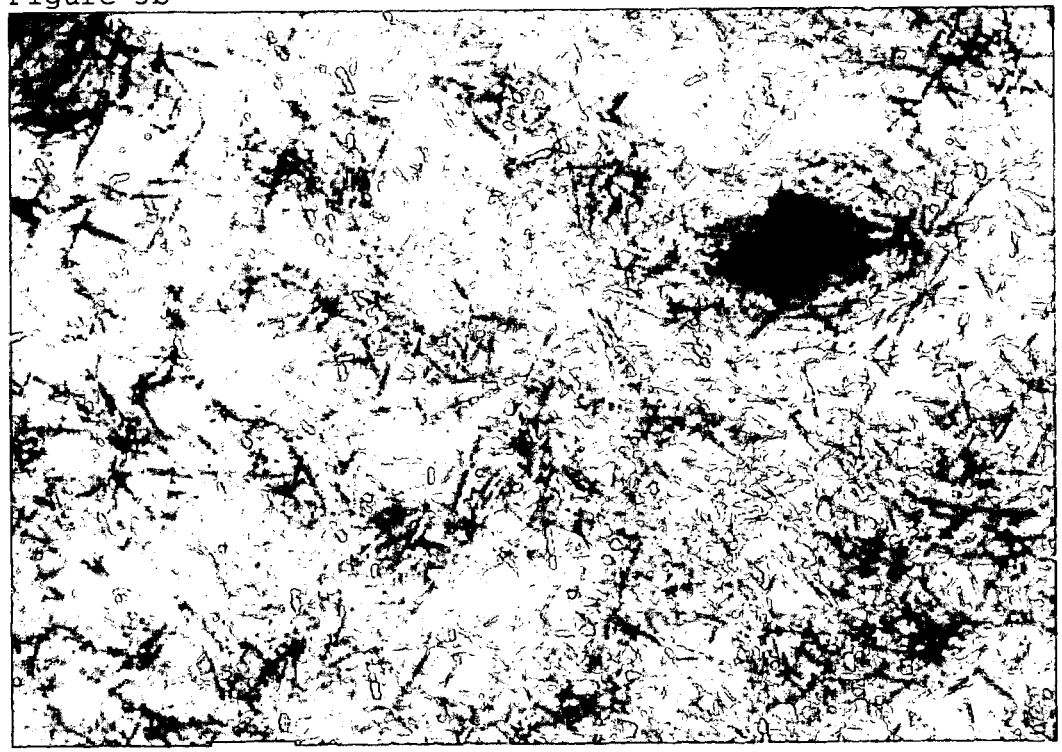
Figure 4A:
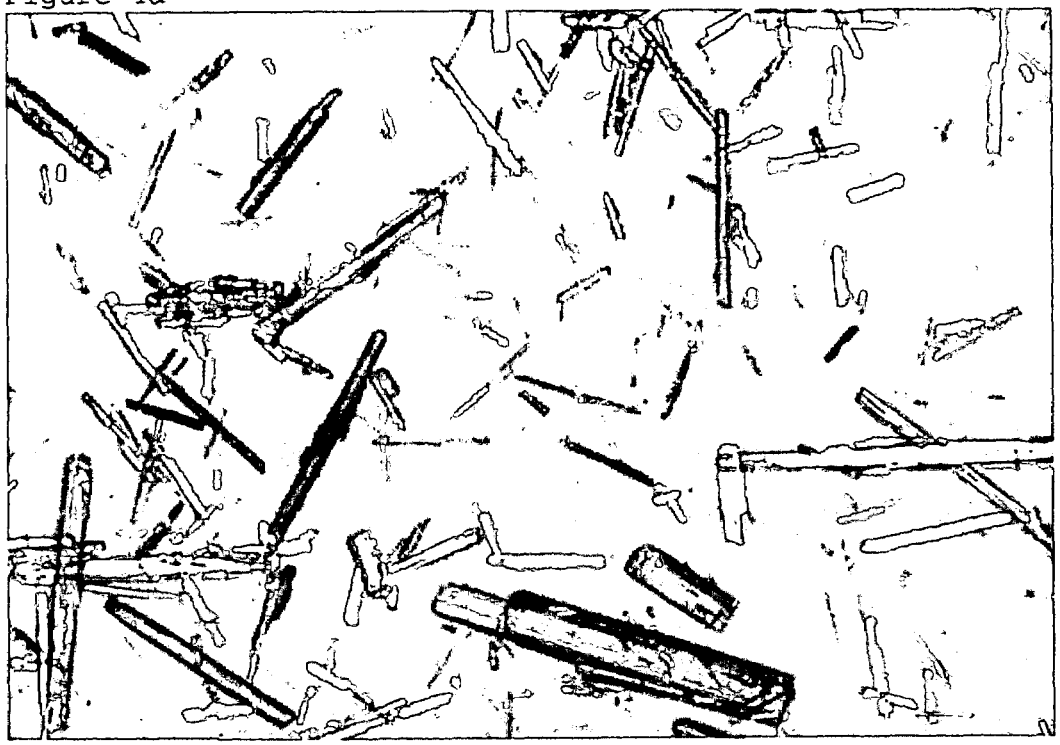
FIGS. 4a-b: Micrographs (100× and 50× magnification, respectively) of rasagiline tartrate crystals prepared according to Example 15.
Figure 4B:
Figure 5A:
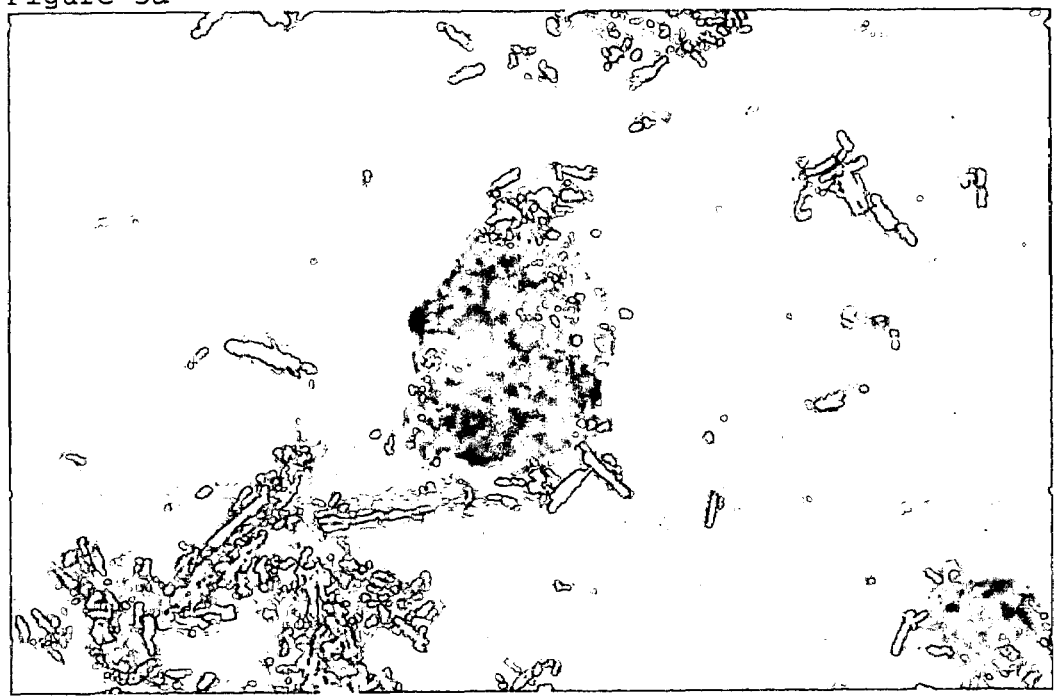
FIGS. 5a-b: Micrographs (150× and 300× magnification, respectively) of ladostigil tartrate crystals prepared according to Example 16.
Figure 5B:
Figure 6A:
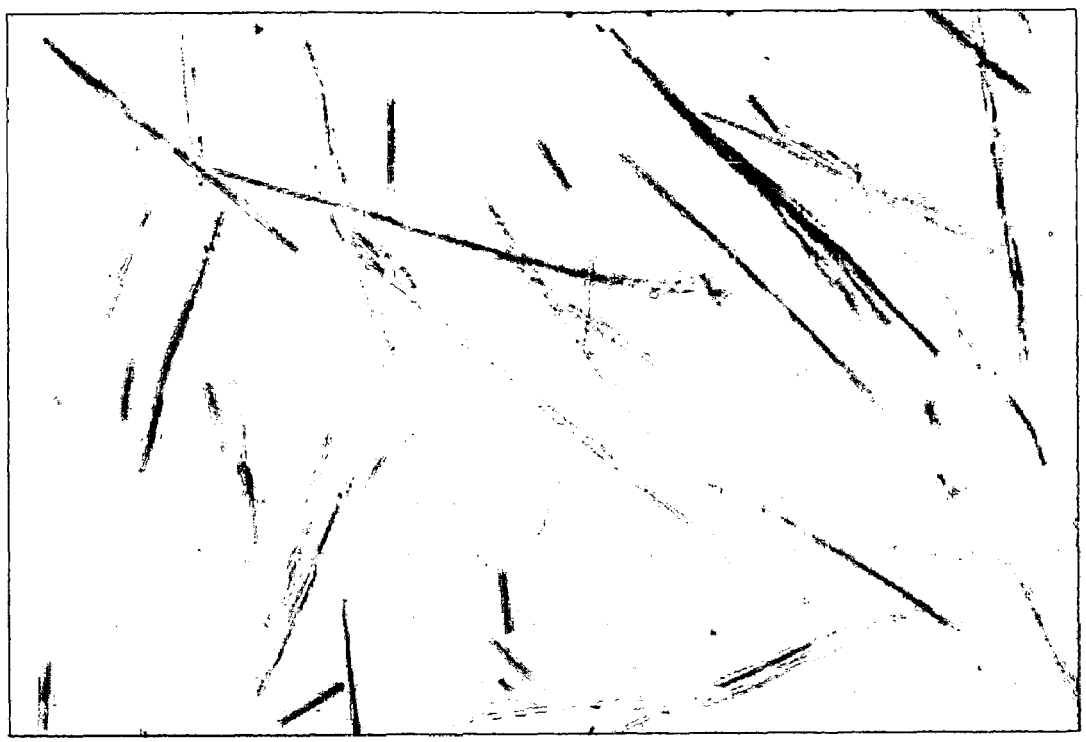
FIGS. 6a-b: Micrographs (100× and 50× magnification, respectively) of rasagiline tartrate crystals prepared according to Example 18.
Figure 6B:
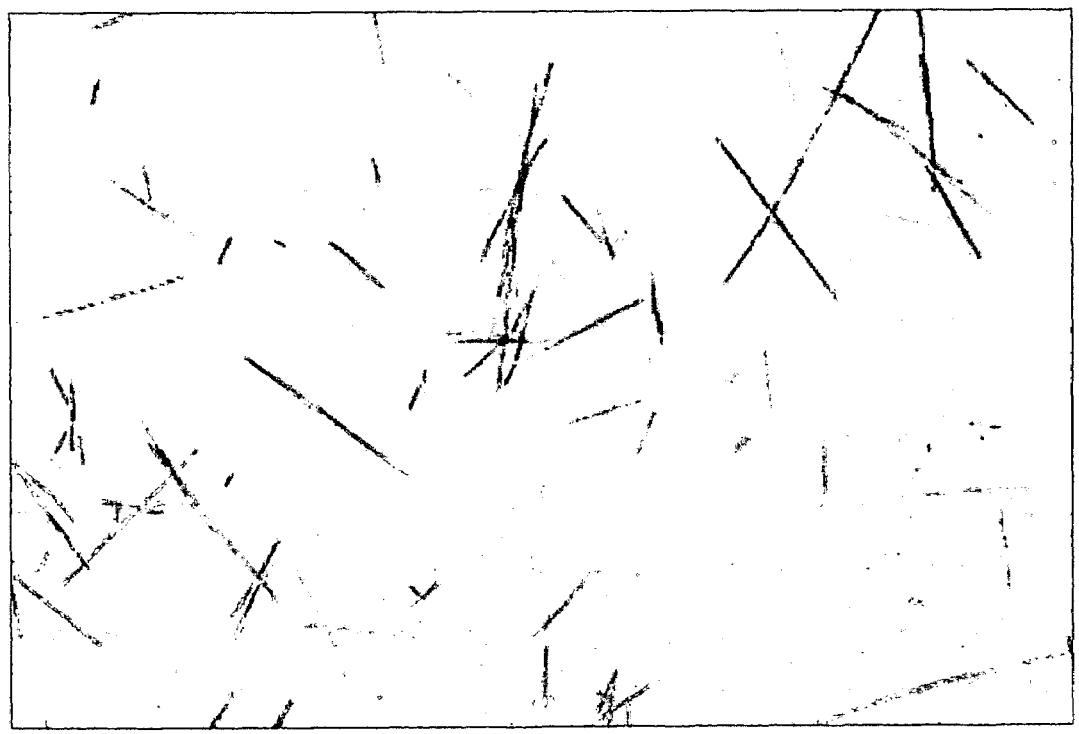
Figure 7A:
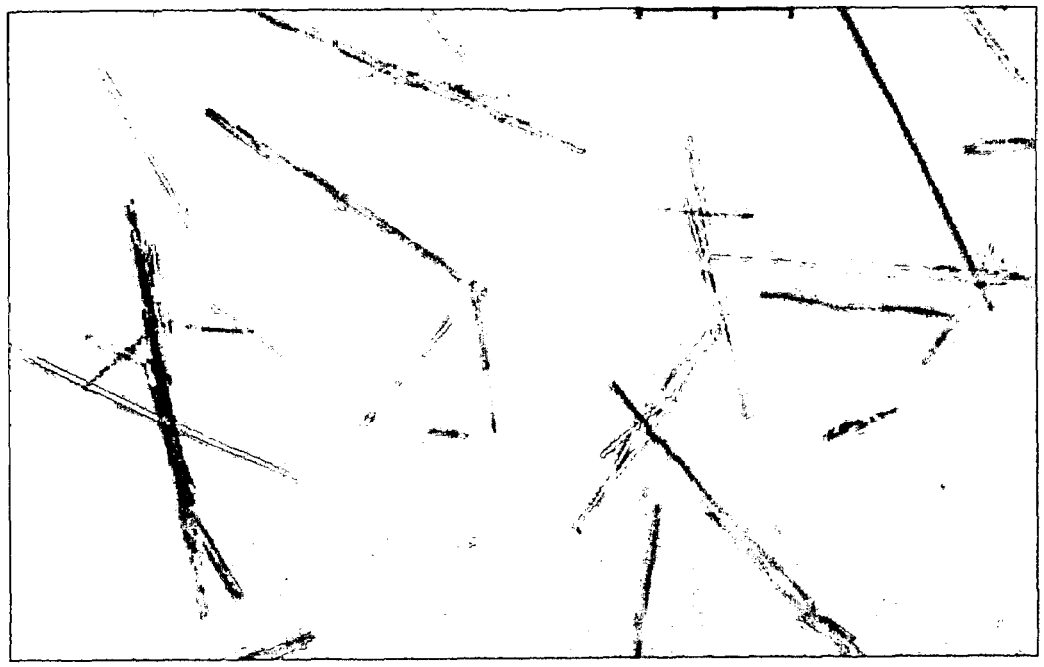
FIGS. 7a-b: Micrographs (100× and 50× magnification, respectively) of rasagiline tartrate crystals prepared according to Example 19.
Figure 7B:
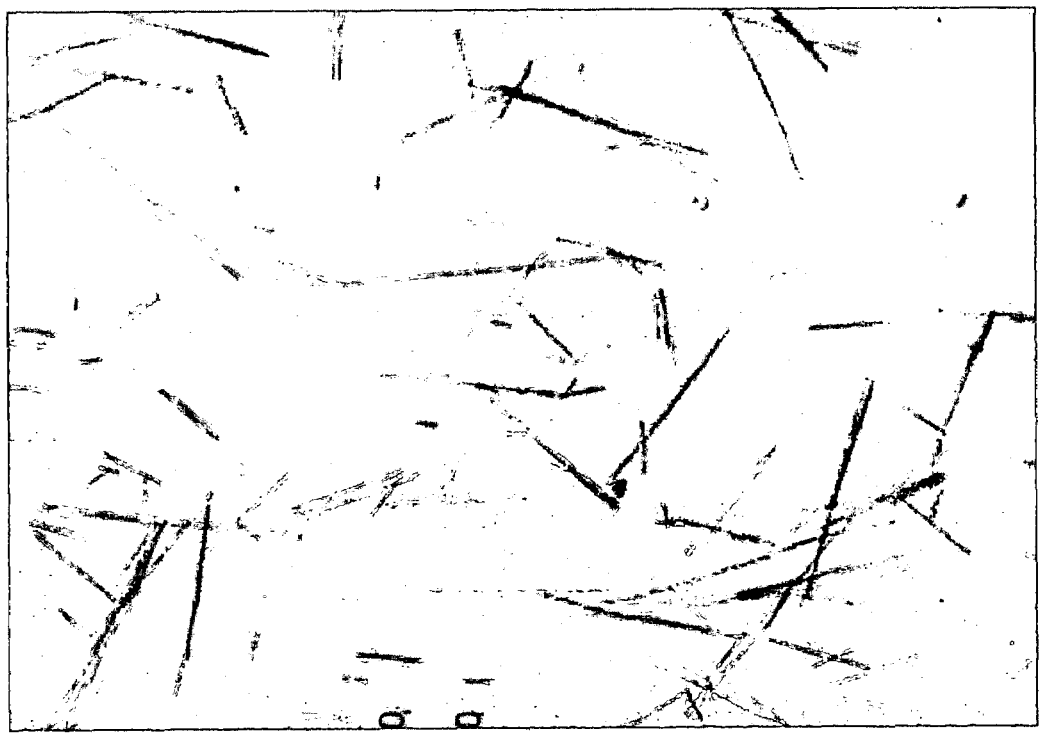

The "water recrystallization method" is represented in FIG. 2 and involves:
adding L-tartaric acid to the reaction mixture in an amount equivalent to one of the enantiomers of the mono-propargylated aminoindan derivative to form a crude salt,
separating the crude mono-propargylated aminoindan derivative tartrate salt from the reaction mixture,
recrystallizing the crude mono-propargylated aminoindan derivative tartrate salt in water to form a pure mono-propargylated aminoindan derivative tartrate salt, and
separating said pure salt from the water.

One advantage of the "water recrystallization method" is that less organic solvent is required than in the prior art methods, and the method does not require disposal of large amounts of acidic solvents.

Another advantage of recrystallization of rasagiline tartrate in water is the production of large, rod-shaped crystals, as opposed to smaller, needle-shaped crystals. The needle-shaped crystals are characterized by aggregation and lower density which reduces their workability. Rod-shaped crystals could provide better processability of the product including flowability of a slurry, solid filterability and improved cake wash.

In addition, needle-shaped crystals have been shown to cause processability problems when making pharmaceutical compositions using conventional tableting devices. For example, needle-shaped crystals are often difficult to coat, thereby precluding their use in controlled release pharmaceutical dosage forms. See, e.g. Rouhi, *Chemical & Engineering News*, Washington, Feb. 24, 2003. Rod-shaped crystals, on the other hand, do not suffer from such limitations.

The methods of the current invention are feasible for scale-up production.

Although water recrystallization is sometimes used to purify crude salts to remove impurities, when used with the primary aminoindans of interest discussed herein, the water recrystallization method unexpectedly provided additional enantiomeric purity. Thus, as seen in Example 14, the water recrystallization method eliminated aminoindan impurity and unexpectedly provided additional enantiomeric purity.

List of abbreviations used in the text:

| | |
|---|---|
| AI | Indan-1-ylamine |
| HPLC | High pressure liquid chromatography |
| m.p. | Melting point |
| PAI | N-Propargyl-1-aminoindan |
| PBS | Propargyl Benzenesulfonane |
| (R)-CAI | Ethyl-methyl-carbamic acid (R)-3-amino-indan-5-yl ester |
| (R)-CPAI | Ethyl-methyl-carbamic acid (R)-3-prop-2-ynylamino-indan-5-yl ester (ladostigil) |
| TLC | Thin layer chromatography |

"Pure", as used herein, refers to the absence of extraneous elements of any kind, to the extent detectable by available techniques.

"Enantiomerically pure", as used herein, refers to a state in which one enantiomer is absent, to the extent detectable by available techniques.

EXPERIMENTAL DETAILS

Extraction Methods—Examples 1-2

Example 1

Rasagiline Tartrate Isolation Using Extraction Method 1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was mixed with 300 ml of water and was stirred. The resulting mixture was acidified with 66% sulfuric acid to a pH of 2.2 and stirring was stopped. The mixture was settled for ½ hour and the lower phase (acidic aqueous layer) was separated. The upper organic phase was discarded.

The aqueous phase was mixed with 250 ml of toluene while stirring and was basified to a pH of 6.3 with a 25% solution of NaOH. After the pH was adjusted to 6.3, the stirrer was stopped and the mixture was allowed to settle. The lower aqueous phase and the upper toluenic phase were separated. The aqueous phase was reintroduced into the reactor, mixed with an additional 200 ml of toluene. The reactor was stirred and the pH was adjusted to 7.0 with a 25% solution of NaOH. After pH adjustment, the stirrer was stopped and the mixture was allowed to settle. The lower aqueous phase was separated and discarded. The organic toluene phase was combined with the organic toluene phase from the previous extraction and was washed with 200 ml water. After the washing and settling, the aqueous layer was separated and the resulting organic toluene phase was evaporated in rotating evaporator under vacuum. After the toluene evaporation, the residue was dissolved in 80 ml isopropanol and the solvent was evaporated under the same conditions. 38.6 g of brown oil (PAI base) resulted. Aqueous solution of L-tartaric acid was prepared by dissolution of 12.36 g of the acid in 19.6 g water.

PAI base was dissolved in 225 ml isopropanol, stirred, heated to reflux and the solution of L-tartaric acid was added to the PAI solution at reflux conditions. The addition resulted in crystallization of solid rasagiline tartrate salt. The suspension was cooled to room temperature, filtered and the solid product was washed on a filter with two portions of isopropanol.

The wet solid product was dried to a constant mass and was analyzed. Yield 24.0 g (28.8%)

Analysis:

m.p. 176.3-176.8° C., Purity by TLC: one spot. Purity by HPLC: AI content 0.1%; S-isomer content: <4%; remainder R-PAI.

Solid morphology: Aggregated small (100-300 micron) needle-shaped crystals.

Example 2

Ladostigil Tartrate Isolation Using Extraction Method 26.3 g of 100% (R)-CAI (in the form of 30.1 g technical grade syrup-like compound) were introduced into a reactor with water (75 ml), toluene (100 ml) and NaOH (34.8 g of 25% solution). 21.4 g of PBS were introduced and stirring was started. The reaction mass was stirred at 45-46° C. for 5 hours. The stirrer was stopped, and the mixture was allowed to settle.

The lower aqueous phase was discarded and the upper organic phase was mixed with 250 ml of water and was stirred. The mixture was acidified with 66% Sulfuric Acid to a pH of 2.0. After the acidification, the stirrer was stopped, and the mixture was allowed to settle. After phase separation, the upper organic layer was discarded and the lower aqueous phase was reintroduced into the reactor.

The acidic aqueous phase was mixed with 200 ml toluene, stirred, and basified with 25% NaOH to a pH of 5.2. The mixture was stirred at 45° C., the stirrer was stopped, and the mixture was allowed to settle. The upper organic phase and the lower aqueous phase were separated and the aqueous phase was reintroduced into the reactor.

150 ml toluene was added, and the pH was adjusted with 25% NaOH solution to 5.2. The mixture was stirred at 45° C., the stirrer was stopped, and the mixture was allowed to settle. The upper organic phase and the lower aqueous phase were separated. The aqueous layer was discarded and the organic layer was combined with the organic phase from the previous separation. The combined organic solution was evaporated under vacuum in a rotating evaporator, the residue was dissolved in 50 ml isopropanol and the solvent was evaporated under the same conditions.

21.8 g of brown oil (R)-CPAI free base resulted. The free base was dissolved in 137 ml isopropanol while stirring in a reactor.

6.0 g of L-tartaric acid were dissolved in 70 ml isopropanol. The reactor was heated and the tartaric acid solution was introduced dropwise into the reactor at 60-65° C.

Crystallization of ladostigil tartrate occurred during the addition of the tartaric acid solution. After the addition was completed, the mixture was cooled to 3° C., and the solid product was filtered and washed with cold isopropanol. Resulting wet ladostigil tartrate was dried under vacuum, sampled and analyzed.

Analysis:

m.p. 145.4-145.7° C., Purity by TLC: one spot ((R)-CPAI). Purity by HPLC: 99.8%; S-isomer content: <0.04%.

Discussion:

Examples 1 and 2 show that extraction can be used to isolate pure (R)-PAI and (R)-CPAI tartrate salts. However, these processes require many steps and require much acidified organic solvent which is difficult to dispose of.

Direct Isolation Processes—Examples 3-5

Example 3

Rasagiline Tartrate Isolation by Direct Precipitation of Rasagiline Tartrate 1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was washed with 70 ml water and was evaporated under vacuum in a rotating evaporator. The residue which resulted was dissolved in 70 ml isopropanol and the solvent was again evaporated under the same conditions.

The resulting brown oil (55.4 g) was dissolved in 205 ml isopropanol while being stirred in a reactor. A solution of 12.6 g L-tartaric acid in 19.7 ml water was prepared.

The reactor with isopropanolic solution was heated to reflux while stirring, and the solution of L-tartaric acid was added dropwise at reflux. A solid product was precipitated during the addition of acid. The resulting suspension was cooled to 25° C., and the solid product was filtered and washed with isopropanol. The wet solid was dried under vacuum. The dry solid product (28.7 g of white crystalline powder) was sampled and analyzed.

Analysis:

m.p. 162.7-163.2° C., Purity by TLC: two spots. Purity by HPLC: AI content 22.6%; S-isomer content: 12%; remainder R-PAI.

Example 4

Rasagiline Tartrate Isolation by Direct Precipitation of Rasagiline Tartrate 1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was washed with 70 ml water and was evaporated under vacuum in a rotating evaporator. The residue which resulted was dissolved in 70 ml isopropanol and the solvent was again evaporated under the same conditions.

The resulting brown oil (56.5 g) was dissolved in 120 ml of isopropanol while being stirred stirring in reactor. An L-tartaric acid solution was prepared by dissolving 12.6 g of L-tartaric acid in 125 ml isopropanol and heating.

The solution in the reactor was heated to reflux while being stirred and then the L-tartaric acid solution was introduced to the reactor dropwise under reflux conditions.

A solid product was precipitated during the addition. The resulting suspension was cooled to 25° C. and the solid product was filtered and washed with isopropanol. The wet solid dried under vacuum. 33.9 g of dry solid product in the form of white crystalline powder was sampled and analyzed.

Analysis:
m.p. 160.8-161.2° C., Purity by TLC—two spots (AI+PAI) Purity by HPLC—AI content 25.6%; S-isomer content 16%

Example 5

Rasagiline Tartrate Isolation by Direct Prolonged Precipitation of Rasagiline Tartrate (Slow Crystallization)

1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was washed with 70 ml water and was evaporated under vacuum in a rotating evaporator. The residue which resulted was dissolved in 70 ml isopropanol and the solvent was again evaporated under the same conditions.

The resulting brown oil (56.5 g) was dissolved in 120 ml isopropanol while stirring in reactor.

8.2 g of L-tartaric acid was dissolved in 19 ml water.

The solution in the reactor was heated to reflux while stirring and the solution of tartaric acid was introduced to the reactor dropwise under reflux conditions.

Solid product was not precipitated during the addition. The resulting mixture was cooled and seeded with rasagiline tartrate at 73° C. The seeding material was not dissolved and at 64° C. crystallization of the batch was observed. The batch was cooled to 25° C. over 12 hours and stirred at this temperature for 6 hours. The solid product was filtered and washed with isopropanol. The wet solid was dried under vacuum. 20.6 g of dry solid product in the form of white crystalline powder was sampled and analyzed.

Analysis:
m.p. 162.9-163.2° C., Purity by TLC—two spots (AI+PAI) Purity by HPLC—AI content 39.8%, PAI content 62.2%; S-isomer content: much greater than 4%. (Note: It was difficult to determine the exact content of S-enantiomer because the broad peak of AI overlapped the peak of the S-enantiomer).

Discussion:
Examples 3, 4 and 5 show that it is difficult to directly separate pure mono-propargylated aminoindan derivative from the reaction mixture. The crude salts produced upon the addition of L-tartaric acid to the reaction mixture are contaminated by primary aminoindan as well as by S-enantiomer.

Aminoindan Crystallization Processes—Examples 6-11

Examples 6-9 relate to rasagiline and Examples 10-11 relate to ladostigil.

Example 6

Rasagiline Tartrate Separation by Aminoindan Tartrate Precipitation and Separation Racemic Aminoindan Tartrate Precipitation 1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was washed with 70 ml water and was evaporated under vacuum in a rotating evaporator. The residue which resulted was dissolved in 70 ml isopropanol and the solvent was again evaporated under the same conditions.

The resulting brown oil (56.5 g) was dissolved in 225 ml isopropanol while stirring in a reactor.

An acidic solution was prepared by dissolving 4.12 g of L-tartaric acid in 6.4 ml water.

The solution in the reactor was heated to reflux at stirring and the solution of tartaric acid was introduced to the reactor dropwise under reflux conditions.

A solid product was precipitated during the addition. The resulting suspension was filtered and the solid product washed with isopropanol. Both the mother liquor filtrate and the isopropanol wash filtrate were collected and saved. The wet solid was dried under vacuum. 7.6 g of dry solid product in the form of white crystalline powder was sampled and analyzed.

Analysis:
m.p. 193.0-195.7° C., Purity by TLC—one spot (AI) Purity by HPLC—PAI content 0.1%. Racemic AI was attained.

Pure Rasagiline Tartrate Crystallization

The filtrates were introduced into a reactor and stirred. An acidic solution was prepared by dissolving 8.24 g of L-tartaric acid was dissolved in 12.9 ml water. The solution in the reactor was heated to reflux while stirring and the solution of tartaric acid was introduced to the reactor dropwise under reflux conditions.

Solid product was precipitated during the addition. The resulting suspension was cooled to 25° C. and the solid product was filtered and washed with isopropanol. The wet solid was dried under vacuum. 23.3 g of dry solid product in the form of white crystalline powder were sampled and analyzed.

Analysis:
m.p. 176.7-177.9° C., Purity by TLC—one spot (R-PAI) Purity by HPLC—AI content 0.4%, S-isomer content—<4%

Example 7

Rasagiline Tartrate Preparation by Aminoindan Sulfate Precipitation and Separation Racemic Aminoindan Sulfate Precipitation 1-aminoindan (45 g), toluene (135 ml), water (85 ml) and NaOH (60 g of 25% solution) were introduced into a reactor, stirred, and PBS (67.5 g) was added at ambient temperature. The reaction mass was heated to 45° C. and held at this temperature for 4 hours.

The stirrer was stopped and the reaction mixture was allowed to settle. After phase separation, the lower aqueous phase was discarded. The upper organic phase was washed with 70 ml water and was evaporated under vacuum in a rotating evaporator. The residue which resulted was dissolved in 70 ml isopropanol and the solvent was again evaporated under the same conditions.

The resulting brown oil (56.5 g) was dissolved in 205 ml of isopropanol while stirring in a reactor. 4.50 g of 66% Sulfuric acid were introduced to the reactor dropwise at ambient temperature.

A solid product was precipitated during the acid addition. The resulting suspension was cooled to 25° C. and the solid product was filtered and washed with isopropanol. Both the mother liquor filtrate and the isopropanol wash filtrate were collected and saved. The wet solid was dried under vacuum. 8.0 g of dry solid product (white crystalline powder) was sampled and analyzed.

Analysis:

m.p. 236.8-239.8° C., Purity by TLC—two spots (AI+PAI) Purity by HPLC—PAI content 1.8%. Racemic AI was attained (crude AI sulfate was obtained by method).

Pure Rasagiline Tartrate Crystallization

The filtrates were introduced into a reactor and stirred. An acidic solution was prepared by dissolving 8.2 g of L-tartaric acid in 13 ml water. The solution in the reactor was heated to reflux while stirring and the solution of tartaric acid was introduced into the reactor dropwise under reflux conditions.

A solid product was precipitated during the addition of the acid. The resulting suspension was cooled until 25° C. and the solid product was filtered and washed with isopropanol. The wet solid was dried under vacuum. 23.4 g of dry solid product in the form of white crystalline powder were sampled and analyzed.

Analysis:

m.p. 177.2-178.5° C., Purity by TLC—one spot. Purity by HPLC—AI content 0.1%, S-isomer content: <4% Pure R-PAI tartrate was attained.

Example 8

Pure 1-aminoindan Tartrate Control Preparation 1 g of pure 1-aminoindan was dissolved in 25 ml isopropanol in a glass flask equipped with a magnetic stirrer and a thermometer. The solution was heated to 40° C. and 0.54 g of L-tartaric acid was added. Crystallization of the salt was observed immediately. The resulting suspension was cooled to 25° C. and filtered. The solid product was washed with isopropanol on filter and dried under vacuum. 1.4 g of dry solid product in the form of white crystalline powder was sampled and analyzed.

Analysis:

m.p. 193.9-194.9° C., Purity by TLC—one spot (AI) Purity by HPLC—PAI content −0.0%. Pure racemic AI tartrate product was attained.

Example 9

Pure 1-aminoindan Sulfate Control Preparation 5 g of pure 1-aminoindan was dissolved in 50 ml isopropanol in a glass flask equipped with a magnetic stirrer and a thermometer. 2.78 g of 66% Sulfuric Acid (1.8 g anhydrous acid) was added dropwise at ambient temperature. Crystallization of salt was observed during the addition. The resulting suspension was stirred for ½ hour at 25° C. and was filtered. Solid product was washed with isopropanol on a filter and was dried under vacuum. 6.7 g of dry solid product in the form of a white crystalline powder was sampled and analyzed.

Analysis:

m.p. 259.8-261.4° C., Purity by TLC—one spot (AI) Purity by HPLC—PAI content—not detected. Pure racemic AI sulfate product was attained.

Discussion:

Examples 8 and 9 provided control compounds for comparison of purity of aminoindan salts. The primary aminoindan salts formed by crystallization from the reaction mixture in examples 6 and 7 were of high purity. These salts could be easily re-used in propargyl aminoindan synthesis, thereby significantly reducing the amount of wasted starting material. The (R)-PAI tartrate salts formed by crystallization from the reaction mixture in examples 6 and 7 were of high purity and high enantiomeric purity. This shows that this method of isolation of (R)-PAI tartrate salts is effective. In addition, it uses fewer steps, uses less solvent, and generates less environmentally-unfriendly waste than the extraction method.

Example 10

Pure (R)-CAI Sulfate Preparation

An aqueous solution of (R)-CAI and sulfuric acid was stirred at room temperature for 48 hrs. Solid salt slowly precipitated. The resulting suspension was filtered. The solid product was washed with isopropanol on a filter and dried under vacuum. 3.0 g of dry solid product in the form of a white crystalline powder was sampled and analyzed.

Analysis:

m.p. 191.3-191.7° C., Purity by TLC—one spot (R-CAI) Purity by HPLC—R-CPAI content: 100%

Example 11

Ladostigil Tartrate Isolation by (R)-CAI Sulfate Precipitation (R)-CAI Sulfate Precipitation 28.1 g of 100% (R)-CAI was introduced into a reactor with water (75 ml), toluene (100 ml) and NaOH (34.8 g of 25% solution). 21.4 g of PBS were introduced while stirring. The reaction mass was stirred at 45-46° C. over 5 hours. The stirrer was stopped, and the mixture was allowed to settle.

The lower aqueous layer was discarded. The upper organic layer was washed with 70 ml water and was evaporated under vacuum in a rotating evaporator. The residue which resulted from evaporation was dissolved in 70 ml isopropanol and the solvent was evaporated under the same conditions.

The resulting brown oil (28 g) was dissolved in 207 ml isopropanol by stirring in a reactor. 1.63 g of 66% Sulfuric Acid (1.08 g anhydrous) was introduced into the reactor dropwise at ambient temperature. The mixture was stirred over 24 hours at 15-25° C., and no solid precipitation was observed. The reactor was seeded at 25° C. with the solid R-CAI Sulfate from example 10. Immediately after the seeding, product crystallization was observed. The resulting suspension was stirred at 25° C. for one hour and was filtered. The solid product was washed with isopropanol on a filter and was dried under vacuum. The mother liquor filtrate and the filtrate from the washing were collected and combined. 6.0 g of dry solid product in the form of white crystalline powder was sampled and analyzed.

Analysis:

m.p. 184.9-186.0° C., Purity by TLC—two spots ((R)-CAI+(R)-CPAI).

Purity by HPLC—(R)-CAI content: 31.7%.

Ladostigil Tartrate Crystallization and Isolation

The filtrates were introduced into a reactor and stirred. The solution in the reactor was heated to reflux while stirring and 6.0 g of solid L-tartaric acid were introduced into the reactor under reflux conditions. A solid product precipitated after the addition of acid. The resulting suspension was cooled to 5° C. and the solid product was filtered and washed with isopropanol. The wet solid was dried under vacuum. 23.4 g of dry solid product in the form of white crystalline powder was sampled and analyzed.

Analysis:

m.p. 146.0-146.1° C., Purity by TLC—one spot ((R)-CPAI) Purity by HPLC—(R)-CAI content: 0.15%.

Discussion:

Example 11 shows that pure ladostigil tartrate can be isolated from a reaction mixture by prior salt formation of (R)-CAI, followed by crystallization of ladostigil tartrate from the mother liquor.

Water Recrystallization Processes—Examples 12-16

Example 12

Rasagiline Tartrate Re-crystallization from Water, Batch A 14.0 g crude rasagiline tartrate (product of Example 5) were mixed with 140 ml of deionized water in a reactor. The batch was stirred and heated to 60° C. and the solids were dissolved. The solution was cooled, and at 40° C. crystallization was observed. The batch was further cooled to 5° C. and filtered. The solid product was washed with ice cold water on a filter and was dried under vacuum. 4.0 g of dry solid product in the form of white crystalline powder was sampled and analyzed.

Analysis:

m.p. 178.3-178.8° C., Purity by TLC—one spot (PAI) Purity by HPLC—AI content: 0.73%.

Optical Purity: Substantially pure rasagiline tartrate with a minor aminoindan impurity was attained.

Example 13

Rasagiline Tartrate Re-crystallization from Water, Batch B

The filtrate and washing liquor from Example 12 were combined and evaporated at 30° C. by passing Nitrogen through the solution while stirring. After evaporation of part of the water, precipitation of solids was observed. The suspension was cooled to 5° C. and filtered. Solid product was washed with ice cold water on a filter and was dried under vacuum. 1.6 g of dry solid product in the form of white crystalline powder was sampled and analyzed.

Analysis:

m.p. 178.3-178.5° C., Purity by TLC—one spot (PAI) Purity by HPLC—AI content: 1.2%.

Optical purity: Substantially pure rasagiline tartrate with a minor aminoindan impurity was attained.

Example 14

Rasagiline Tartrate Re-crystallization from Water 24.5 g of crude rasagiline tartrate (from Example 3) were mixed with 120 ml of deionized water in a reactor. The suspension was stirred and heated to 80° C. and the solids were dissolved. The resulting solution was cooled, and at 50° C. crystallization was observed. The batch was further cooled to 5° C. and was filtered. The solid product was washed with ice cold water on the filter and was dried under vacuum. 14.5 g of dry solid product in the form of white crystalline powder was sampled and analyzed.

Analysis:

m.p. 177.8-179.1° C., Purity by TLC—one spot (PAI) Purity by HPLC—AI content: 0.3%.

Optical Purity: Substantially pure rasagiline tartrate with a minor aminoindan impurity was attained.

Example 15

Pure Rasagiline Tartrate Re-crystallization from Water 9.3 g rasagiline tartrate were mixed with 150 ml deionized water in reactor. The reactor was stirred and heated to 65° C. During the heating the solids were dissolved. The resulting solution was cooled, and at 46° C. crystallization was observed. The batch was cooled to 5° C. and filtered. Solid product was washed with ice cold water on a filter and dried under vacuum. 4.0 g of dry solid product in the form of white crystalline powder was sampled and analyzed.

Analysis:

m.p. 177.9-178.6° C., Purity by TLC—one spot (PAI)

Purity by HPLC—AI content: not detected. Pure rasagiline tartrate was attained.

Example 16

Ladostigil Tartrate Re-crystallization from Water 13.8 g of Ladostigil Tartrate mixed with 11.5 g of deionized water and stirred at heating. At 60° C. complete dissolution of solids was observed and the resulting solution was cooled, seeded at 50° C. and then cooled to 20° C. Crystallization took place after the seeding. The crystals were separated from the mother liquor by filtration, washed with isopropanol and dried under vacuum. 5.35 g of solid Ladostigil Tartrate was obtained, yield 38.8%.

Analysis:

m.p. 145.0-145.6° C.

Discussion:

The results of these examples show that it is possible to achieve enantiomeric purity by recrystallization of rasagiline tartrate, and ladostigil tartrate, from water.

Non-diastereomeric Salt Forms of the Aminoindan Derivatives

Once the desired compounds are isolated using the chiral acid as discussed herein, the salt form can be easily changed to any desirable salt which may not be a diastereomeric salt. In this manner, any salt form of an aminoindan derivatives of interest of the desired optical purity can be prepared using the processes disclosed herein. For example, R-PAI mesylate can be prepared using the disclosed processes.

Example 17

Conversion of Rasagiline Tartrate to Rasagiline Mesylate

Isolation of Rasagiline Base 59.0 g of wet rasagiline tartrate were mixed with 109.0 g water, and sodium hydroxide (31.5 g of 25% solution) was added. The mixture was stirred and 135 g of Toluene were added. Then the resulting mixture was settled, and the lower aqueous layer was separated and discarded. The upper organic layer was washed twice with water (65 ml and 20 ml) and the solvent was evaporated under vacuum on water bath. The residue after evaporation was dissolved in 56 g of isopropanol and the solvent was evaporated under the same conditions. 29.3 g of rasagiline free base were obtained as a yellow oil.

Preparation of Rasagiline Mesylate

The residue after evaporation (rasagiline base) was dissolved in 214.5 g of isopropanol and 20.4 g of methanesulfonic acid were added over 10 minutes while stirring and cooling. During the addition crystallization of rasagiline mesylate took place. The resulting suspension was heated while stirring to reflux, and after complete dissolution of solids, was cooled to 10° C. Upon cooling, rasagiline mesylate was crystallized. The mixture was stirred at 10° C. for 15 minutes and filtered. Solid product was washed on a filter with fresh isopropanol and dried under vacuum at 60° C. 41.0 g of dry rasagiline mesylate were obtained.

Aspect Ratio of Crystals

As used herein, "aspect ratio" is the quotient of the division of a crystal's length by its width. The aspect ratio of crystals can be obtained by taking micrographs of a batch of crystal. Each micrograph was then divided into five fields. The length and width of 20 representative crystals in each field was measured. The aspect ratio of each crystal was calculated by dividing the crystal length by the crystal width. The average aspect ratio for each batch was determined by dividing the sum of crystal aspect ratios by the number of crystals measured. The results are reported as an average of at least two measurements per sample.

As noted above, water recrystallization after direct crystal formation but in the substantial absence of impurities produces large, rod-shaped crystals, as opposed to smaller, needle-shaped crystals. The needle-shaped crystals are characterized by aggregation and lower density which reduces their workability. Big, rod-shaped crystals provide better processability of the product including flowability of a slurry, solid filterability and improve cake wash. In addition, needle-shaped crystals have been shown to cause processability problems when making pharmaceutical compositions using conventional tableting devices. For example, needle-shaped crystals are often difficult to coat, thereby precluding their use in controlled release pharmaceutical dosage forms. See, e.g. Rouhi, *Chemical & Engineering News*, Washington, Feb. 24, 2003. Rod-shaped crystals, on the other hand, do not suffer from such limitations.

Examples 17 and 18, below, were performed to recreate known processes of production of rasagiline tartrate through crystallization in a mixture of methanol and t-butylmethyl ether and through recrystallization in methanol/isopropanol (1:1) following the disclosure of U.S. Pat. No. 6,630,514, issued Oct. 7, 2003 to Youdim. The resulting crystals were then compared to the crystals produced by the processes disclosed herein.

Example 18

Rasagiline Tartrate Re-crystallization from Methanol/Isopropanol (1:1)

An example was designed to produce crystals as described in U.S. Pat. No. 6,630,514, example 6B, step b.

18.5 g of Rasagiline Tartrate were suspended in 500 ml of methanol-isopropanol mixture (1:1). The suspension was heated to boiling while stirring. An additional 280 ml of the same mixture of solvents were added under reflux conditions until complete dissolution of solids was observed.

The resulting solution was cooled, and at 63° C. the beginning of crystallization was observed. The batch was cooled to 17° C. and filtered. The product was washed on a filter with a methanol-isopropanol mixture (1:1) and dried under vacuum. 16.7 g of white crystalline powder dry solid product was sampled and analyzed.

Analysis:

m.p. 176.2-177.3° C., Purity by TLC—one spot (PAI) R-PAI tartrate final product was attained.

Example 19

Rasagiline Tartrate Crystallization from Methanol/t-butylmethyl Ether

An example was designed to produce crystals as described in U.S. Pat. No. 6,630,514, example 6A.

A first solution of 5.0 g of L-tartaric Acid in 55 ml methanol was prepared and heated to reflux. Then, a solution of 5.7 g of (R)-PAI in 55 ml methanol was added to the first solution while heating and stirring.

322 ml of t-butylmethyl ether was added to the resulting mixture under reflux conditions over 20 minutes. Crystallization of rasagiline tartrate took place during the addition.

The batch was cooled to 17° C. and filtered. The solid product was washed on a filter with t-butylmethyl and dried under vacuum. Dry solid product (7.6 g white crystalline powder) was sampled and analyzed.

Analysis:

m.p. 176.4-178.4° C., Purity by TLC—one spot (PAI) R-PAI tartrate final product was attained.

Example 20

Measurement of Aspect Ratio of Rasagiline Tartrate Produced by Various Methods Slides were prepared and micrographs were taken from each batch of each example as listed below in table 1. Each micrograph was divided into five fields. The length and width of 20 representative crystals in each field were measured. The aspect ratio of each crystal was calculated by dividing the crystal length by the crystal width. The average aspect ratio for each batch was determined by dividing the sum of crystal aspect ratios by the number of crystals measured. The results are reported as an average of at least two measurements per sample.

TABLE 1

| Sample | Based on Example: | Aspect ratio | Particle morphology |
|---|---|---|---|
| A | 15 | 10 | Rods |
| B | 1 | 15 | Needles |
| C | 19 | 21 | Needles |
| D | 18 | 22 | Needles |

It is evident from Table 1 that the known methods of crystallization and recrystallization, as shown in examples 1, 18, and 19, produced needle-shaped crystals with higher aspect ratio than the rod-shaped crystals produced using water-recrystallization according to this invention. Thus, the direct isolation process as disclosed herein results in crystal of improved aspect ratio while also being less complex and more economical.

What is claimed is:

1. A process for isolating from a reaction mixture a salt of a mono-propargylated aminoindan having the structure

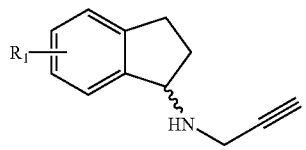

wherein $R_1$ is H, hydroxyl, alkoxy or

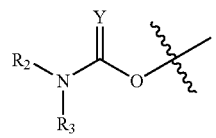

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a primary aminoindan having the structure

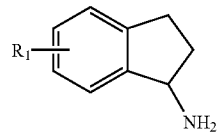

wherein $R_1$ is defined as above, and a tertiary aminoindan having the structure

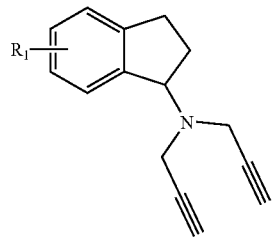

the process comprising
a) adding an acid to the reaction mixture;
b) crystallizing the mono-propargylated aminoindan under conditions suitable for the formation of a crystalline salt of the mono-propargylated aminoindan; and
c) recovering the crystalline salt of the mono propargylated aminoindan,
wherein the process is performed without addition of an organic solvent.

2. The process of claim 1, wherein step a) comprises: 1) adding a first acid to the reaction mixture in an amount sufficient to form a crystalline acid addition salt of the primary aminoindan; and
2) removing the crystalline acid addition salt of the primary aminoindan from the reaction mixture, thereby separating the primary aminoindan from the mono-propargylated aminoindan and the tertiary aminoindan.

3. The process of claim 1, wherein step b) comprises addition of a second acid to the reaction mixture under conditions suitable for the formation of the crystalline salt of mono-propargylated aminoindan.

4. A process for isolating from a reaction mixture a diastereomeric salt of a mono-propargylated aminoindan having the structure

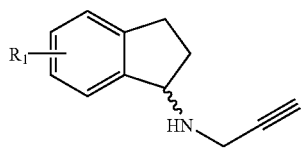

wherein $R_1$ is H, hydroxyl, alkoxy or

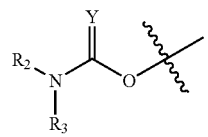

wherein Y is O or S; $R_2$ and $R_3$ is each, independently, $C_{1-8}$ alkyl, $C_{6-12}$ aryl, $C_{6-12}$ aralkyl, each optionally halo substituted, or hydrogen;

where the reaction mixture further comprises a solvent, a racemic primary aminoindan having the structure

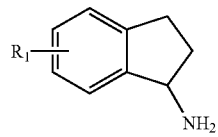

wherein $R_1$ is defined as above, and a racemic tertiary aminoindan having the structure

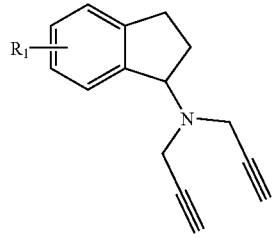

said process comprising
a) adding a first acid to the reaction mixture in an amount sufficient to form a crystalline acid addition salt of the primary aminoindan;

b) removing the crystalline acid addition salt said of the primary aminoindan from the reaction mixture, thereby separating the primary aminoindan from the reaction mixture;

c) adding a second acid to the reaction mixture under conditions suitable for the formation of the crystalline salt of mono-propargylated aminoindan; and d) recovering the crystalline salt of the mono-propargylated aminoindan.

5. The process of claim 2 wherein the first acid is added in a quench amount to the primary aminoindan in the reaction mixture.

6. The process of claim 5, wherein the first acid is sulfuric acid or tartaric acid.

7. The process of claim 1 wherein the solvent in the reaction mixture is isopropanol.

8. The process of claim 2 wherein the crystalline acid addition salt of the primary aminoindan is removed by filtration.

9. The process of claim 1 further comprising a step of washing the crystalline salt of the mono-propargylated aminoindan.

10. The process of claim 1, wherein step a) comprises:
  1) adding a chiral acid to the reaction mixture in an amount equivalent to the mono-propargylated aminoindan to form a crude diastereomeric salt of the mono-propargylated aminoindan; and
  2) separating the crude diastereomeric salt of the mono-propargylated aminoindan from the reaction mixture.

11. The process of claim 10, wherein step b) comprises recrystallization of the crude diastereomeric salt of mono-propargylated aminoindan in water.

12. A process for isolating from a reaction mixture a diastereomeric salt of a mono-propargylated aminoindan having the structure

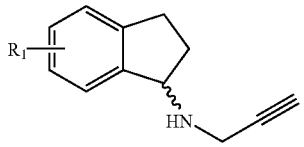

wherein R$_1$ is H, hydroxyl, alkoxy or

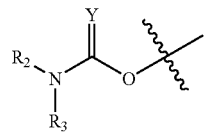

wherein Y is O or S; R$_2$ and R$_3$ is each, independently, C$_{1-18}$ alkyl, C$_{6-12}$ aryl, C$_{6-12}$ aralkyl, each optionally halo substituted, or hydrogen;

where the reaction mixture further comprises a solvent, a racemic primary aminoindan having the structure

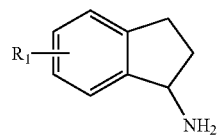

wherein R$_1$ is defined as above, and a racemic tertiary aminoindan having the structure

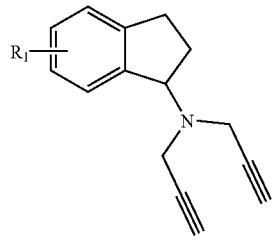

said process comprising a) adding a chiral acid to the reaction mixture in an amount equivalent to the mono-propargylated aminoindan derivative to form a crude diastereomeric salt of the mono-propargylated aminoindan;

b) separating the crude diastereomeric salt of the mono-propargylated aminoindan from the reaction mixture;

c) recrystallizing the crude diastereomeric salt of the mono-propargylated aminoindan in water to isolate crystalline diastereomeric salt of the mono-propargylated aminoindan; and d) recovering crystalline diastereomeric salt of the mono-propargylated aminoindan.

13. A process for isolating from a reaction mixture a salt of enantiomerically pure N-propargyl-1-aminoindan or a salt of enantiomerically pure 6-(N-methyl, N-ethyl-carbamoyloxy)-N'-propargyl-1-aminoindan, wherein the reaction mixture further comprises a primary aminoindan having the structure

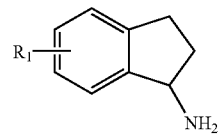

wherein R$_1$ is H or

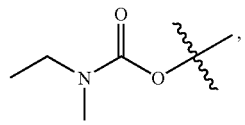

and a tertiary aminoindan having the structure

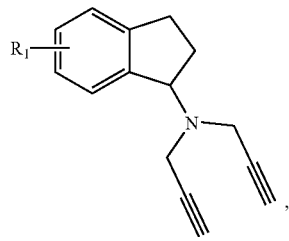

the process comprising crystallizing the salt of enantiomerically pure N-propargyl-1-aminoindan or the salt of enantiomerically pure 6-(N-methyl, N-ethyl-carbamoyloxy)-N'-propargyl-1-aminoindan, wherein the process is performed without addition of an organic solvent.

14. The process of claim 13, wherein the enantiomerically pure N-propargyl-1-aminoindan is R(+)-N-propargyl-1-aminoindan, and the enantiomerically pure 6-(N-methyl, N-ethyl-carbamoyloxy)-N'-propargyl-1-aminoindan is R(+)-6-(N-methyl, N-ethyl-carbamoyloxy)-N'-propargyl-1-aminoindan.

15. The process of claim 14, wherein the salt of R(+)-N-propargyl-1-aminoindan is the tartrate salt and the salt of R(+)-6-(N-methyl, N-ethyl-carbamoyloxy)-N'-propargyl-1-aminoindan is the tartrate salt.

16. Crystalline diastereomeric salt of the mono-propargylated aminoindan prepared by the process of claim 10 having an aspect ratio of less than 15.

17. A pharmaceutical composition comprising crystalline diastereomeric salt of the mono-propargylated aminoindan prepared by the process of claim 10 having an aspect ratio of less than 15.

18. Crystalline rasagiline tartrate salt having an aspect ratio of less than 15.

19. The crystalline rasagiline tartrate salt of claim 18 having an aspect ratio of less than 12.

20. A pharmaceutical composition comprising crystalline rasagiline tartrate salt having an aspect ratio of less than 15.

21. The process of claim 1, wherein $R_1$ is H.
22. The process of claim 2, wherein $R_1$ is H.
23. The process of claim 4, wherein $R_1$ is H.
24. The process of claim 6, wherein $R_1$ is H.
25. The process of claim 10, wherein $R_1$ is H.
26. The process of claim 12, wherein $R_1$ is H.

27. The process of claim 10, wherein the chiral acid is L-tartaric acid and the diastereomeric salt is the L-tartrate salt.

28. The process of claim 27, wherein the mono-propargylated aminoindan tartrate salt is pure.

29. The process of claim 28, wherein the mono-propargylated aminoindan tartrate salt is enantiomerically pure.

30. The process of claim 10, further comprising converting the mono-propargylated aminoindan diastereomeric salt into a mesylate salt.

31. The process of claim 27, further comprising converting the mono-propargylated aminoindan diastereomeric salt into a mesylate salt.

32. The process of claim 28, further comprising converting the mono-propargylated aminoindan diastereomeric salt into a mesylate salt.

33. The process of claim 29, further comprising converting the mono-propargylated aminoindan diastereomeric salt into a mesylate salt.

34. The process of claim 30, wherein the mono-propargylated aminoindan diastereomeric mesylate salt is rasagiline mesylate.

35. The process of claim 31, wherein the mono-propargylated aminoindan diastereomeric mesylate salt is rasagiline mesylate.

36. The process of claim 32, wherein the mono-propargylated aminoindan diastereomeric mesylate salt is rasagiline mesylate.

37. The process of claim 33, wherein the mono-propargylated aminoindan diastereomeric mesylate salt is rasagiline mesylate.

* * * * *